(12) United States Patent
MacDonald

(10) Patent No.: US 8,182,800 B2
(45) Date of Patent: *May 22, 2012

(54) METAL ION MODIFIED HIGH SURFACE AREA MATERIALS FOR ODOR REMOVAL AND CONTROL

(75) Inventor: John Gavin MacDonald, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 237 days.

This patent is subject to a terminal disclaimer.

(21) Appl. No.: 12/546,755

(22) Filed: Aug. 25, 2009

(65) Prior Publication Data

US 2009/0318287 A1 Dec. 24, 2009

Related U.S. Application Data

(62) Division of application No. 10/137,052, filed on Apr. 30, 2002, now Pat. No. 7,578,997.

(51) Int. Cl.
*A01N 25/34* (2006.01)

(52) U.S. Cl. .............. 424/76.9; 2/901; 95/273; 422/5; 424/49; 424/65; 424/402; 424/404; 424/421; 424/489; 424/618; 424/630; 424/635; 424/641; 424/646; 424/647; 424/648; 424/649; 424/691; 442/381; 442/394; 442/402; 428/34.1; 428/375; 428/402; 604/359; 977/773; 977/779; 977/810; 977/904; 977/961

(58) Field of Classification Search .................. None
See application file for complete search history.

(56) References Cited

U.S. PATENT DOCUMENTS

| | | | |
|---|---|---|---|
| 3,013,897 | A | 12/1961 | Cupery et al. |
| 4,172,781 | A | 10/1979 | Walk et al. |
| 4,313,820 | A | 2/1982 | Farha, Jr. et al. |
| 4,525,410 | A | 6/1985 | Hagiwara et al. |
| 4,725,415 | A | 2/1988 | Kidd |
| 4,775,585 | A | 10/1988 | Hagiwara et al. |
| RE32,957 | E | 6/1989 | Elias |
| 4,836,141 | A | 6/1989 | Whitfield |
| 4,988,505 | A | 1/1991 | Watanabe et al. |
| 5,064,599 | A | 11/1991 | Ando et al. |
| 5,102,592 | A | 4/1992 | McCauley et al. |

(Continued)

FOREIGN PATENT DOCUMENTS

CA 2350757 A1 5/2000

(Continued)

OTHER PUBLICATIONS

Malik et al., *Characterisation of novel modified active carbons and marine algal biomass for the selective adsorption of lead*, Water Research 36, 2002, pp. 1527-1538.

(Continued)

*Primary Examiner* — Neil Levy
(74) *Attorney, Agent, or Firm* — Dority & Manning, P.A.

(57) ABSTRACT

This invention relates to high surface area materials, such as nanoparticles, that are coated with metal ions. These modified nanoparticles have active sites that bind various gases and/or odorous compounds, thereby removing these compounds from a medium such as air or water. Metal ions are adsorbed onto the surface of the nanoparticle and bound strongly to the surface. By selection of the metal ion, specific gaseous compounds and/or odorous compounds can be targeted and removed efficiently and effectively from both aqueous phase and from the air. The modified nanoparticles are useful in numerous article of manufacture for industrial and consumer use.

26 Claims, 3 Drawing Sheets

U.S. PATENT DOCUMENTS

| | | | |
|---|---|---|---|
| 5,108,739 A | 4/1992 | Kurihara et al. |
| 5,120,693 A | 6/1992 | Connolly et al. |
| 5,122,418 A | 6/1992 | Nakane et al. |
| 5,180,585 A | 1/1993 | Jacobson et al. |
| 5,183,656 A | 2/1993 | Uesaka et al. |
| 5,407,442 A | 4/1995 | Karapasha |
| 5,429,628 A | 7/1995 | Trinh et al. |
| 5,480,636 A | 1/1996 | Maruo et al. |
| 5,486,356 A | 1/1996 | Yim |
| 5,534,249 A | 7/1996 | Maurer |
| 5,580,655 A | 12/1996 | El-Shall et al. |
| 5,595,750 A | 1/1997 | Jacobson et al. |
| 5,663,224 A | 9/1997 | Emmons et al. |
| 5,843,267 A | 12/1998 | Cashaw et al. |
| 5,861,144 A | 1/1999 | Peterson et al. |
| 5,874,067 A | 2/1999 | Lucas et al. |
| 5,882,638 A | 3/1999 | Dodd et al. |
| 5,885,262 A | 3/1999 | Wheeler |
| 5,885,599 A | 3/1999 | Peterson et al. |
| 5,948,398 A | 9/1999 | Hanamoto et al. |
| 6,096,299 A | 8/2000 | Guarracino et al. |
| 6,254,894 B1 | 7/2001 | Denkewicz, Jr. et al. |
| 6,299,867 B1 | 10/2001 | Aoyagi et al. |
| 6,344,218 B1 | 2/2002 | Dodd et al. |
| 6,410,616 B1 | 6/2002 | Harada et al. |
| 6,447,373 B1 | 9/2002 | Lack et al. |
| 6,858,147 B2 | 2/2005 | Dukhin et al. |
| 6,926,862 B2 | 8/2005 | Fotenot et al. |
| 7,141,518 B2 | 11/2006 | MacDonald et al. |
| 7,238,403 B2 | 7/2007 | Koslow et al. |
| 7,371,456 B2 | 5/2008 | Nohr et al. |
| 7,438,875 B2 | 10/2008 | Do et al. |
| 7,488,520 B2 | 2/2009 | Urlaub et al. |
| 7,678,367 B2 | 3/2010 | McGrath et al. |
| 2001/0023338 A1 | 9/2001 | Guarracino et al. |
| 2001/0031248 A1 | 10/2001 | Hall-Puzio et al. |
| 2002/0005145 A1 | 1/2002 | Sherman |
| 2002/0096518 A1 | 7/2002 | Foster, Sr. |
| 2002/0132070 A1 | 9/2002 | Franzen et al. |
| 2002/0141898 A1 | 10/2002 | Carlucci et al. |
| 2003/0078552 A1 | 4/2003 | Tepper et al. |
| 2003/0226773 A1 | 12/2003 | Shaffer |
| 2005/0084412 A1 | 4/2005 | MacDonald et al. |
| 2005/0112085 A1 | 5/2005 | MacDonald et al. |
| 2005/0181067 A1 | 8/2005 | Yokoyama et al. |

FOREIGN PATENT DOCUMENTS

| | | |
|---|---|---|
| CN | 1287878 | 3/2001 |
| DE | 10116192 | 10/2002 |
| EP | 0251783 A2 | 1/1988 |
| EP | 0572914 A1 | 12/1993 |
| EP | 1053788 A1 | 11/2000 |
| EP | 0684075 | 3/2003 |
| WO | WO0029311 A1 | 5/2000 |
| WO | WO0189411 A1 | 11/2001 |
| WO | WO0226272 A1 | 4/2002 |
| WO | WO02098747 A2 | 12/2002 |
| WO | WO02098747 A3 | 12/2002 |
| WO | WO02098765 A1 | 12/2002 |
| WO | WO03092885 A1 | 11/2003 |
| WO | WO2004079075 A1 | 9/2004 |
| WO | WO2006111402 A2 | 10/2006 |

OTHER PUBLICATIONS

Park et al., *Dimerization of tert-butylmercaptan over the surface of aerosol impregnated with copper and manganese*, Bulletin of the Korean Chemical Society, 21(7), 2000, pp. 715-719, CAPLUS abstract # 133:270673.

METAL ION MODIFIED HIGH SURFACE AREA MATERIALS FOR ODOR REMOVAL AND CONTROL

RELATED APPLICATIONS

The present application is a divisional of U.S. application Ser. No. 10/137,052 filed on Apr. 30, 2002, now U.S. Pat. No. 7,578,997, which is incorporated herein in its entirety by reference thereto.

FIELD OF THE INVENTION

This invention relates to modified high surface area materials useful in neutralizing or removing gases and/or odorous compounds. The high surface area material, such as a nanoparticle, is coated with metal ions that can bind with gas molecules and/or odorous compounds. The modified high surface area materials can be incorporated into various industrial and consumer products including absorbent articles, air and water filters, household cleaners, fabrics, and paper towels.

BACKGROUND OF THE INVENTION

Many attempts have been made to formulate an effective odor removal system and various consumers products are available for combating odorous compounds. Some products are designed to cover up odors by emitting stronger, more dominant odors, examples including scented air freshener sprays and candles. Another way to combat odorous compounds, including ammonia, methyl mercaptan, trimethylamine, and other various sulfides and amines, is to remove these compounds from a medium by deodorizing agents that will absorb these compounds.

Activated charcoal and sodium bicarbonate are two compounds commonly used to absorb odors. However, activated charcoal typically has a low deodorizing ability, especially for ammonia odors and when in the presence of moisture, and the black color of charcoal lacks aesthetically pleasing characteristics desired in absorbent articles such as diapers. Sodium bicarbonate, and other white odor absorbents such as silica gel and zeolites, generally have a lower absorbency than activated charcoal and are therefore less effective.

Titanium oxide particle, such as taught in U.S. Pat. No. 5,480,636 issued to Maruo et alt, are also useful in removing a few odors such as ammonia. U.S. Pat. No. 5,480,636 teaches adding zinc oxy or silicon oxy compounds to the titanium oxide to broaden the titanium oxide deodorizing capabilities. However, this approach is still limited by the photocatalytic nature of the titanium dioxide which requires light in order to convert odorous compounds into non-odorous compounds. Also the titanium oxide compounds as disclosed in U.S. Pat. No. 5,480,636 are not useable in aqueous solutions.

In addition to foul smelling compounds, there is a need for products capable of removing gases that, while not necessarily odorous, still cause a negative effect. One example of such a gaseous compound is ethylene. Ethylene, a natural hormone, is released by fruits as a ripening agent. By removing ethylene gas, fruit ripening could be slowed and controlled, allowing for extended storage and transportation.

There is a need for a gas and/or odor removal/neutralizing compound that is effective both dry and in solution. There is a need for an effective odor removal/neutralizing compound that can be used in various industrial and consumer products. There is a need for a gas and/or odor removal/neutralizing compound that can be easily applied to various surfaces and materials.

SUMMARY OF THE INVENTION

This invention relates to high surface area materials that are coated with metal ions. These modified high surface area materials have active sites that bind at least one gaseous compound and/or odorous compound, thereby removing these compounds from a medium such as air or water. Nanoparticles are a type of high surface area materials useful in this invention to remove at least one of gaseous compounds and odorous compounds. At least one type of metal ion is adsorbed onto the surface of the nanoparticle and bound strongly to the surface. By selection of the metal ion, certain gaseous compounds and/or odorous compounds can be targeted and removed efficiently and effectively from both aqueous phase and from the air. This invention uses high surface area nanoparticles as templates to adsorb specific functionalities (metal ions) that target at least one of gaseous compounds and odorous compounds and form complexes with them and remove them from the media. For example, silica nanoparticles modified by copper ions (or alternatively, silver ions) were demonstrated to be effective in removing amine and sulfur based classes of odorous compounds.

It is one object of this invention to create an effective gaseous compound removal system. The invention is useful in various industrial and consumer products. It is another object of this invention to create a gaseous compound removal system for inhibiting the ripening of plant materials.

It is another object of this invention to create an effective odor removal compound useful in both aqueous phase and in the air. It is another object of this invention to create an effective odor removal compound that can effectively be used in various industrial and consumer products. This invention can be used in combination with various products for the removal of odors. Modified high surface area materials of this invention are useful in absorbent articles such as diapers and feminine products for removing odors. Modified high surface area materials of this invention are useful in filtration devices and coated onto walls, wall paper, and glass for removal of odors. Modified high surface area materials of this invention are useful in oral care products such as mouthwash and chewing gum for the removal of compounds in the mouth that cause unpleasant odors.

The foregoing and other features and advantages will become further apparent from the following detailed description of the presently preferred embodiments read in conjunction with the drawings.

DETAILED DESCRIPTION OF THE PRESENTLY PREFERRED EMBODIMENTS

This invention relates to high surface area materials, such as nanoparticles, modified with at least one metal ion. The modified high surface area materials of this invention are useful in removing gaseous compounds and/or odorous compounds. "Gaseous compound" or "gas" includes any molecule or compound that can exist as a gas or vapor. "Odorous compound" or "odor" refers to any molecule or compound detectable to the olfactory system. Odorous compounds can exist as a gaseous compound and can also be present in other media such as liquid.

The high surface area materials of this invention have at least one metal ion present on the surface of the high surface area material, and the metal ion creates an active site that binds with at least one gaseous compound and/or odorous compound thereby removing the compound from the surrounding environment. High surface area materials can also absorb certain gaseous compounds and/or odorous compounds from the surrounding environment by adsorption directly onto the surface area of the high surface area materials.

Gas and/or odor removing particles of this invention are modified high surface area materials. High surface area materials useful in this invention have a large surface area due to the small size of the individual particles of the high surface area material. High surface area materials useful in this invention have a suitable surface area of at least about 200 square meters/gram, more suitably 500 square meters/gram, and more suitably 800 square meters/gram.

Figure 1:
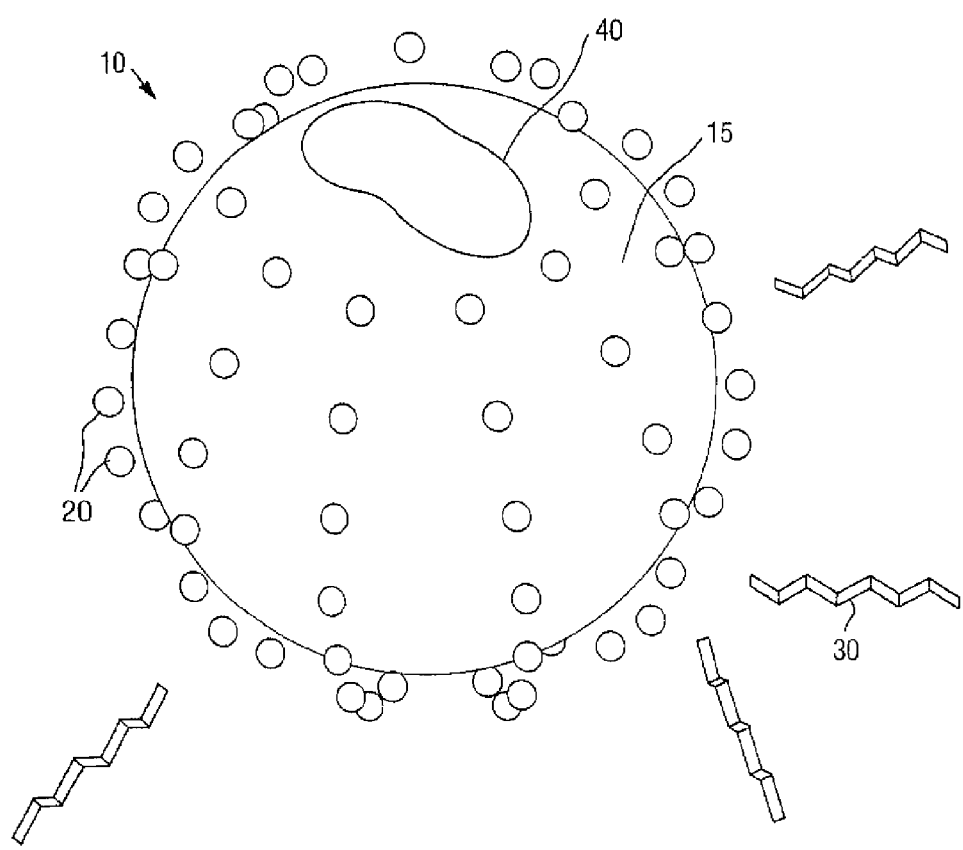
FIG. 1 is a drawing of a modified nanoparticle according to one embodiment of this invention.

Nanoparticles are examples of high surface area materials useful in this invention. "Nanoparticle" refers to a high surface material having a particle diameter of less than about 500 nanometers. While the invention will be described hereinafter with particular reference to nanoparticles, it will be understood that the invention is useful with various high surface area materials. FIG. 1 shows a modified a nanoparticle 10 according to one embodiment of this invention, useful as a gas and/or odor removing particle. The modified nanoparticle 10 includes a nanoparticle 15 and metal ions 20. FIG. 1 shows a plurality of metal ions 20, however modified nanoparticle 10 can have various amounts of metal ions 20 and will have at least one metal ion 20. The modified nanoparticle 10 is useful for removing various gaseous compounds and/or odorous compounds. The specific compound to be removed is generally dependent on the specific metal ions 20 used and the type of nanoparticle 15.

Nanoparticles useful in this invention include, without limitation, silica, alumina, magnesium oxide, titanium dioxide, iron oxide, gold, zinc oxide, copper oxide, organic nanoparticles such as polystyrene, and combinations thereof. Nanoparticles are not generally ionic yet still have an overall electric Zeta Potential. "Zeta Potential" refers to the electrical potential, or electrokinetic potential, that exists across the interface of all solids and liquids. Nanoparticles with either positive or negative Zeta Potentials are known. Naturally occurring chemical reactions on the surface of a nanoparticle result in the Zeta Potential of that nanoparticle. For example, silica nanoparticles are tetrahedral complexes of silicon dioxide molecules. On the surface of the silica particles the silicon dioxide molecules can undergo chemical reactions forming silanol groups (SiOH) the silanol groups reacting with other silanol groups to form siloxane bonds (Si—O—Si bonds). The dehydration reactions of the silanol groups to form the silanol bond and the reverse reactions result in a negative Zeta Potential and allow positively charged metal ions to adsorb onto the silica.

The nanoparticles useful in this invention will typically have a first Zeta Potential and a second Zeta Potential after adsorption of the metal ion onto the nanoparticle due to the addition of the oppositely-charged metal ions. The Zeta Potential change of the nanoparticle is related to the amount of metal ions adsorbed onto the nanoparticle. This relationship provides a measurement for determining the amount of adsorbed metal ions and a method for controlling the amount of adsorption. For instance, the addition of a dilute solution of copper chloride dropwise to a silica nanoparticle solution until the Zeta Potential of the silica suspension changed from −25 millivolts to a higher Zeta Potential, such as in the range of about −5 millivolts to −15 millivolts, was found to be provide a sufficient concentration of metal ions adsorbed onto the nanoparticles to remove particular odorous compounds. In one embodiment of this invention the nanoparticle has a difference between the first and second Zeta Potential of at least about 1.0 millivolt and suitably at least about 5.0 millivolts.

The nanoparticles of this invention are modified with metal ions that ionically bond with compounds such as gases and odorous compounds. "Metal ion" refers to salt ions and/or ion complexes of transition metal elements designated as IB through VIIIB on the periodic table. Other ions can be used in the invention as well. Metal ions are adsorbed onto high surface area materials due to differences in electric potential. Positively charged metal ions are adsorbed onto a negatively charged surface of a nanoparticle and vice versa. Examples of metal ions useful in this invention include, without limitation, copper ion ($Cu^{+2}$), silver ion ($Ag^{+1}$), gold ion ($Au^{+1}$ and $Au^{+3}$), iron (II) ion ($Fe^{+2}$), iron (III) ion ($Fe^{+3}$), permanganate ion ($MnO_4^{-1}$), and combinations thereof.

In one embodiment of this invention the nanoparticle useful in this invention has a negative Zeta Potential and adsorbs positively charged metal ions. One suitable nanoparticle has a negative Zeta Potential of about −1 to −50 millivolts and suitably about −1 to −20 millivolts. In one embodiment of this invention the nanoparticle having a negative Zeta Potential is a silica nanoparticle. Silica nanoparticles useful in this invention are available from Nissan Chemical Industries, Ltd., Houston, Tex., under the name SNOWTEX®, have a particle size range of 1-100 nanometers. The silica nanoparticle can be modified with a positively charged metal ion such as copper ions, silver ions, gold ions, iron ions, and combinations thereof.

In another embodiment of this invention the nanoparticle useful in this invention has a positive Zeta Potential and adsorbs negatively charged metal ion complexes. One suitable nanoparticle has a positive first Zeta Potential of about 1 to 70 millivolts and suitably about 10 to 40 millivolts. In one embodiment of this invention the nanoparticle having a positive Zeta Potential is an alumina nanoparticle. Alumina nanoparticles are also available from Nissan Chemical Industries, Ltd., Houston, Tex., under the name ALUMINASOL®, and have size ranges of about 1-300 nanometers. The alumina nanoparticle can adsorb negatively charged metal ions and metal ion complexes such as permanganate ions.

Current odor control materials such as activated charcoal or sodium bicarbonate rely on the surface area to absorb certain odors. Using these materials is not as effective at odor removal than the modified high surface area materials of this invention. The addition of a metal ion adsorbed onto the surface of a nanoparticle, as in this invention, provides an active site for capturing and neutralizing gases and odorous compounds. In addition, the modified nanoparticles of this invention still have the large surface area that is useful in absorbing other odorous compounds. The metal ion active sites of the modified nanoparticles are particularly useful in removing odorous compound such as mercaptans, ammonia, amines, and mono- and di-sulfides. Other odorous compounds such as aliphatic ketones, carboxylic acids, aliphatic aldehydes, and aliphatic terpenoids can be removed by adsorption onto the large surface area of the modified nanoparticles. Modified nanoparticles are useful in removing odors caused by sulfides, disulfides, trisulfides, thiols, mercaptans, ammonia, amines, isovaleric acid, acetic acid, propionic acid, hexanal, heptanal, 2-butanone, 2-pentanone, 4-heptanone, and combinations thereof. Modified nanoparticles can also remove gases such as ethylene gas, carvone, dienals, and terpenoids.

More than one type of metal ion can be coated on a nanoparticle. This has an advantage in that certain metal ions may be better at removing specific gases and/or odorous compounds than other metal ions. In one embodiment of this invention more than one type of metal ion are adsorbed onto a nanoparticle for more effectively removing more than one type of gaseous compound or odorous compound from a medium. In one embodiment of this invention more than one type of metal ion are adsorbed onto a nanoparticle for removing at least one gaseous compound and at least one odorous compound from a medium.

Modified nanoparticles of this invention can be used in combination with other modified nanoparticles for effective removal of various gases and odors. In one embodiment of this invention copper ion modified silica nanoparticles are used in combination with permanganate ion modified magnesium oxide nanoparticles. By using the two different modified nanoparticles in combination, numerous odorous compounds can be removed. For example, the modified silica nanoparticle is useful for removing sulphur and amine odors and the modified magnesium oxide nanoparticle is useful in removing carboxylic acid odors. Combining modified nanoparticles of this invention allow for removal of a broader range of odors.

Modified nanoparticles are made by mixing nanoparticles with solutions containing metal ions. Such solutions are generally made by dissolving metallic compounds into a solvent resulting in free metal ions in the solution. The metal ions are drawn to and adsorbed onto the nanoparticles due to the electric potential differences. The Zeta Potential of a nanoparticle changes after the adsorption of metal ions according to this invention. Thus the Zeta Potential can be used to monitor the adsorption of metal ions onto the nanoparticle.

Modified high surface area materials according to this invention are versatile and can be used alone or in combination with other articles of manufacture for effective odor removal and control. Unlike activated charcoal deodorants, the modified nanoparticles of this invention maintain their odor neutralizing effects in solution. The modified nanoparticles of this invention also maintain odor neutralizing properties when dry and in aerosol form. This versatility allows for uses in various commercial products. Other advantages of the modified nanoparticles are that they are colorless in solution and white in powder form (activated charcoal is typically black). Modified high surface area materials of this invention can also be used in combination with other commercially available odor removal materials.

Modified nanoparticles of this invention can be applied to various materials. In one embodiment of this invention modified nanoparticles are held onto a surface of a material by the electrical potential differences between the modified nanoparticle (Zeta Potential) and the material surface (Streaming Potential).

Modified nanoparticles of this invention can be applied as a solution to a surface and dried resulting in a surface that absorbs gas and/or odors. In one embodiment of this invention the modified nanoparticles are used in air filters, such as house filters, vent filters, disposable face masks, and face mask filters. In another embodiment the modified nanoparticles can be applied to walls, wallpaper, glass, toilets, and/or countertops. For instance, the modified nanoparticles can be used in a restroom facility. Other uses include without limitation refrigerator mats and fabric softener sheets.

In one embodiment of this invention the modified nanoparticle is coated onto a fibrous cloth. Various types of fibrous cloths are useful in this invention including, without limitation, cloth made from natural fibers such as wood pulp fibers, cotton fibers, and other plant fibers, and nonwoven webs including spunbond webs, meltblown webs, carded fiber webs, air laid webs, and the like, made from thermoplastic materials such as polyolefin (e.g. polyethylene and polypropylene homopolymers and copolymers), polyesters, polyamines, and the like. Modified nanoparticles can be coated on various types of fabric, film, or fibers. Modified nanoparticles can be coated in various amounts depending on need. Suitably, modified nanoparticles are coated on fabrics, films, or fibers in an amount of about 0.001 to 10.0 grams per square meter and more suitably about 0.1 grams per square meter.

In another embodiment of this invention, the modified nanoparticle are used to absorb gases that plants produce to ripen fruit. Ethylene gas is produced by plants as a hormone to aid fruit ripening. By removing ethylene gas as it is produced, fruit ripening can be slowed and controlled. Permanganate ion modified alumina nanoparticles are useful in removing ethylene gas. In one embodiment the permanganate ion modified alumina nanoparticles are adsorbed onto spunbond polypropylene fabric. The fabric has a negative streaming potential and the positively charged nanoparticles are held strongly onto the fiber surface. The fabric can then be used in packaging and storing fruit such as bananas to inhibit ripening by removing ethylene gas. The fabric can be used to wrap the fruit, as a bag to hold the fruit, or swatches can be included in the current packaging. The modified nanoparticles can also be sprayed onto a box or other packaging material used in transportation and storage of fruit. In one embodiment the cloth has a purple color due to the permanganate ions, and when the fabric is saturated with ethylene the fabric changes to a brown color. This color change acts as an indicator that the fabric needs replacement.

Modified nanoparticles of this invention are useful in removing odorous compounds from solutions such as water and urine. The modified nanoparticles could be applied to water treatment systems for use in removing sulphurous compounds from well water or in toilet tanks to reduce the odors resulting from urine. The modified nanoparticles of this invention are so effective against removing offensive components in urine that the yellow color often present in urine is neutralized, leaving a clear liquid. The modified nanoparticles of this invention could also be used in liquid detergents and household cleaners to remove odors.

In one embodiment of this invention the modified nanoparticles are applied to an absorbent article. The term "absorbent article" includes without limitation diapers, training pants, swim wear, absorbent underpants, baby wipes, adult incontinence products, feminine hygiene products, absorbent tissues, medical garments, underpads, bandages, absorbent drapes, and medical wipes, as well as industrial work wear garments. In one embodiment the modified nanoparticles can be added to the absorbent material of these products. In another embodiment the modified nanoparticles can be applied as a coating on any fabric or film layer, such as the inner liner or outer cover of a diaper. In one embodiment the modified nanoparticles can be applied as a coating on a breathable film of an outer cover of an absorbent article such as a diaper or incontinence product to absorb odors. The modified nanoparticles can also be applied to paper towels and wet wipes for use in cleaning odorous liquids. The absorbent articles absorb the odorous liquid and the modified nanoparticles bind the odorous compounds from the liquid neutralizing the smell.

In another embodiment of this invention, the nanoparticles are used as aerosol odor neutralizers/deodorants. The modified nanoparticles are packaged with a propellant that allows spraying the modified nanoparticles into the air for removal of gases and odorous compounds. The modified nanoparticles can be used in a household air freshener or be used in combination with a mist emitted from a vaporizer or humidifier.

The modified nanoparticles can be used in oral care. Sulphur and amine compounds are often the reason for bad breath. Modified nanoparticles can be added to oral care products such as mouth washes, oral-care chewing gums, toothpaste and/or toothbrush fibers. Using a silica nanoparticle modified with copper ions would be one such modified nanoparticle useful in oral care. Silica is widely used in toothpastes as an abrasive and the modified nanoparticles typically contain small levels of copper ions, far below levels in multiple vitamin tablets. Thus there should not be a health concerns with this use of the modified nanoparticles.

The modified nanoparticles are also useful as a breath indicator. Modified nanoparticles can be used as a color indicator in the presence of odorous compounds. In one embodiment of this invention a cellulose wipe coated with copper ion modified silica nanoparticles is placed in a plastic tube such as a straw. When the user breathes into the straw the cellulose wipe turns from green to blue indicating odors such as ammonia vapor or sulfur compounds. A color change can occur with even a low amount of odorous compounds.

Example 1

A dilute suspension of modified silica nanoparticles was made by adding 1 milliliter of SNOWTEX C®, available from Nissan Chemical Industries, Ltd., Houston, Tex., to 9 milliliters of deionized water. The suspension was pipetted in equal portions into four cuvets. Solutions of 0.01 percent by weight of each of copper chloride ($CuCl_2$), silver nitrate ($AgNO_3$), and zinc chloride ($ZnCl_2$), all from Aldrich Chemical Company, Milwaukee, Wis., were prepared and one drop of each was added to a separate cuvet. The Zeta Potential of all four suspension was then measured by a Zetapals Unit, available from Brookhaven Instruments Corp., Holtsville, N.Y. The Zeta potential of the SNOWTEX C control suspension was measured to be −25 millivolts. The Zeta potential of both the SNOWTEX C/copper chloride suspension and the SNOWTEX C/silver nitrate suspension were measured to be −11 millivolts. The Zeta potential of the SNOWTEX C/zinc chloride suspension was measured to be −8 millivolts. The difference in Zeta Potential between the solutions was evidence that the metal ions had absorbed onto the silica nanoparticle.

Figure 2A:
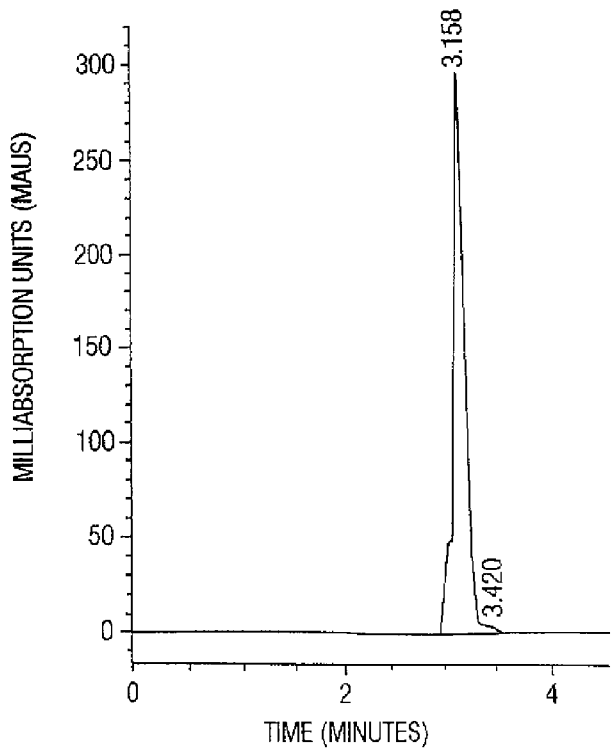
FIG. 2A is a high performance liquid chromatography chromatogram.

A furfuryl mercaptan solution was prepared for testing the odor removal properties of the modified silica nanoparticles. A stock solution of 0.001 percent by weight furfural mercaptan solution, available from Aldrich Chemical Co., Milwaukee, Wis., was made in distilled water. The solution had a strong odor. High performance liquid chromatography (HPLC) was used to measure concentration changes. A Zorbax Eclipse XDB-C18, 4.6 by 150 millimeter, 5 micron column was used along with 100 percent acetonitrile eluent. One microliter of the furfuryl mercaptan solution was injected into the HPLC column with a flow rate of 0.25 milliliters/minute. FIG. 2A, the generated HPLC chromatogram, shows furfuryl mercaptan peak to have an area of 16918 milliabsorption units.seconds (maus).

Figure 2B:
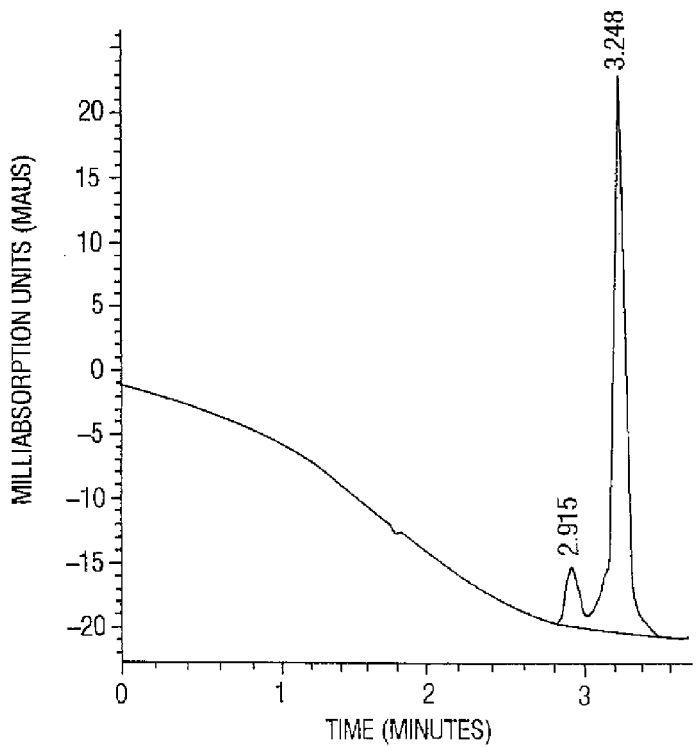
FIG. 2B is a high performance liquid chromatography chromatogram.

One drop of the SNOWTEX C/copper ion suspension was then added to 10 milliliters of the furfuryl mercaptan solution. The furfuryl mercaptan odor rapidly disappeared and one microliter of this furfuryl mercaptan solution was injected into the HPLC column with a flow rate of 0.25 milliliters/minute. FIG. 2B, the generated HPLC chromatogram, shows the furfuryl mercaptan peak to have an area of 188 milliabsorption units.seconds (maus). The concentration of the furfuryl mercaptan was greatly reduced, and the detectable odor as well, with the addition of the modified nanoparticles.

Example 2

Figure 3A:
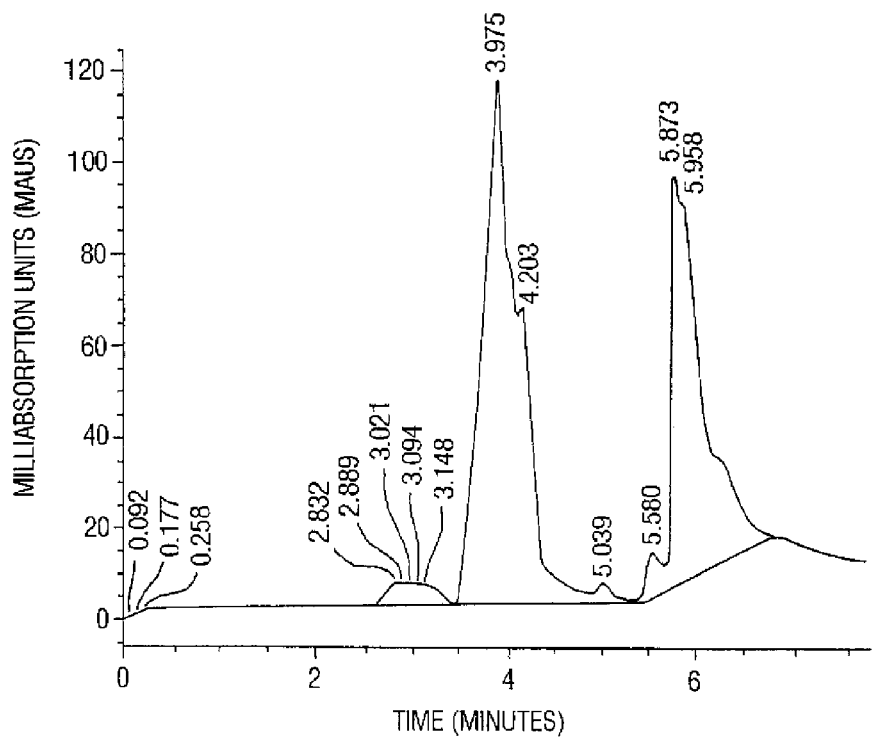
FIG. 3A is a high performance liquid chromatography chromatogram.
Figure 3B:
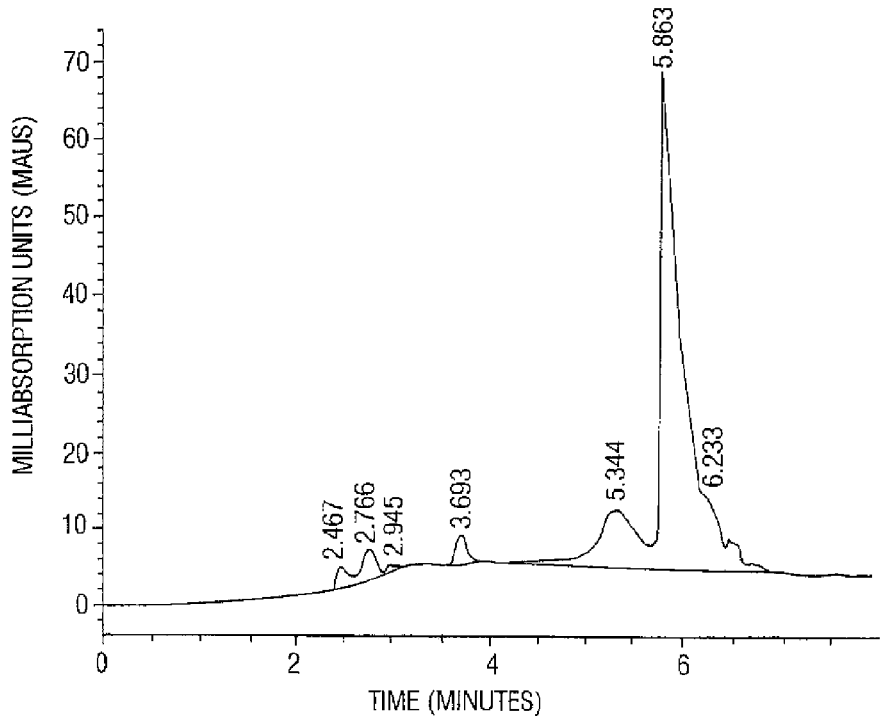
FIG. 3B is a high performance liquid chromatography chromatogram.

The SNOWTEX C/copper ion suspension was tested on human urine to determine the effectiveness in odor reduction. HPLC, as described in Example 1, was used to measure the components of urine (obtained from the inventor). One drop of the SNOWTEX C/copper ion suspension from Example 1 was tested against 0.1 gram of Purite Micronet MN-150 latex particles, available from Purolite Company, Philadelphia, Pa., and 0.1 gram of activated charcoal, available from Aldrich Chemical Co., Milwaukee, Wis. Each of these were added to a separate 3 grams of urine. The urine odor of the sample with the SNOWTEX C/copper ion suspension was almost completely eliminated after 3-5 seconds, compared to about 10 minutes for the activated charcoal. The latex particles never did remove the odor. FIG. 3A shows the HPLC chromatogram of the urine sample and FIG. 3B shows the chromatogram of the urine sample after the modified silica nanoparticles were added. Table 1 summarized the comparison of the HPLC peaks for the 4 samples. The modified silica nanoparticles performed substantially better in removing the urine components then the present commercial materials.

TABLE 1

| | Urine component HPLC peaks (peak retention time (minutes)) | | | | | |
|---|---|---|---|---|---|---|
| Sample | area of peak at 3.87 min. | area of peak at 4.04 min. | area of peak at 4.77 min. | area of peak at 5.64 min. | area of peak at 5.88 min. | area of peak at 6.23 min. |
| Urine | 924 maus | 345 maus | 50 maus | 17 maus | 829 maus | 228 maus |
| Urine + Modified Silica Nanoparticles | 0 | 0 | 12 maus | 0 | 701 maus | 2 maus |
| Urine + Purite Latex Particles | 773 maus | 300 maus | 0 | 17 maus | 820 maus | 156 maus |
| Urine + Activated Charcoal | 900 maus | 0 | 50 maus | 17 maus | 820 maus | 10 maus |

Example 3

The odor removal properties of a modified nanoparticle when dry and coated on a surface was tested by coating a 10.16 centimeter square one-ply HI-COUNT® paper towel, available from Kimberly-Clark Corporation, Neenah, Wis., with the SNOWTEX C/copper ion suspension of Example 1 further diluted by 50 percent. The paper towel was coated by dipping the paper towel sample into the suspension. The wet paper towel was air-dried on a sheet of glass. The dried towel was placed over the mouth of a 100 milliliter beaker and held by a rubber band. The beaker contained 20 milliliter of the 0.001 percent by weight furfuryl mercaptan solution. A second untreated control HI-COUNT® paper towel was placed over an identical beaker as a control. The odors from the furfuryl mercaptans penetrated the untreated paper towel. However, no odors penetrated the paper towel treated with the modified nanoparticles for about three hours. After three hours the modified nanoparticles were saturated and the odors were detectable. The treated paper towel developed a dark area over the beaker during testing resulting from the binding of the furfuryl mercaptans.

Example 4

The odor removing properties of modified nanoparticles as an invisible coating on a bathroom tile was tested by treating a standard bathroom tile (15 centimeter×15 centimeter) from Home Depot with copper modified silica nanoparticles of Sample 1. The suspension of copper modified silica nanoparticles was applied to a KIM-WIPE®. The moist KIM-WIPE® was used to wipe the bathroom tile surface and a second dry KIM-WIPE® was used to wipe off any excess liquid. 3.6 microliters of ammonia, 28 percent ammonia in water, available from Aldrich Chemical Co., Milwaukee, Wis., was introduced to a laboratory desiccator via syringe and after 10 minutes an aliquot of the air/odor was sampled and analyzed to determine the concentration of ammonia in the desiccator. The experiment was repeated three times; once with no tile in the desiccator, once with an untreated control tile in the desiccator, and once with the modified nanoparticle treated tile in the desiccator. The ammonia gas was measured by use of a Drager tube, available from SKC, Inc., Pennsylvania, which could measure ammonia in air concentrations from 2 to 30 parts per million. A volume of 60 milliliters of the air/odor was pulled out of the desiccator by means of a syringe. The Drager tube was connected by Tygon tubing between the desiccator and the syringe. The ammonia concentration in the desiccator was measured at 20 parts per million with no tile and with the untreated tile. The ammonia concentration in the desiccator with the modified nanoparticle treated tile was measured at less than 2 parts per million. The modified nanoparticles on the standard bathroom tile were effective in substantially reducing ammonia gas and odor.

Example 5

The following experiment was performed to demonstrate the use of modified nanoparticles of this invention in extending the shelf life of fruit. Permanganate modified alumina nanoparticles were adsorbed onto a 5.0 centimeter by 5.0 centimeter piece of 2 ounce spunbond polypropylene fabric at a level of 0.01 percent modified nanoparticle weight/fabric weight. The amount of permanganate ion was approximately 0.0001 percent ion weight/nanoparticle weight, monitored by measuring the change in nanoparticle Zeta Potential. Each of three yellow bananas with no brown spots from the same bunch were placed into an airtight bag. In the first airtight bag the modified nanoparticle treated fabric was placed. In the second bag contained an untreated 5.0 centimeter square spunbond polypropylene fabric as a control. The third bag contained no fabric piece also as a control. The three airtight bags were stored at ambient temperature for four weeks. At the end of four weeks the bananas in the two control bags were completely black, soft to the touch, and oozing liquid. The banana in the bag with the modified nanoparticle treated fabric was firm to the touch and had only a few brown markings. This demonstrated that the ripening process was slowed by the modified nanoparticles.

Example 6

To demonstrate the odor removing properties of modified organic nanoparticle of this invention copper ions were adsorbed onto polystyrene nanoparticles. A dilute suspension of modified polystyrene nanoparticles was made by adding 1.0 milliliter of polystyrene nanoparticle suspension, the nanoparticles having a particle diameter of 64 nanometers, available from Polysciences, Inc., Warrington, Pa., to 9.0 milliliters of deionized water. The polystyrene nanoparticle suspension had a Zeta Potential of −49 millivolts, as measured by the Zetapals Unit as in Example 1. Two drops of 0.01 percent by weight copper chloride ($CuCl_2$) solution was added to the polystyrene nanoparticle suspension. After the addition of the 2 drops of copper chloride solution the Zeta Potential of the polystyrene solution was measured at −16 millivolts, thus confirming copper ion adsorption onto the polystyrene nanoparticles. One drop of the modified nanoparticle solution was added to a 2.0 milliliters of 0.001 percent by weight solution of furfuryl mercaptan. High performance liquid chromatography as described in Example 1 was used to measure furfuryl mercaptan presence before and after adding the modified nanoparticles. The area of the furfuryl mercaptan peak before the addition of the modified nanoparticles was 193 milliabsorption units and after the addition of the modified nanoparticles was 14 milliabsorption units. The copper modified polystyrene nanoparticles are useful in removing sulphurous compounds.

Example 7

A dilute suspension of modified silica nanoparticles was made by adding 1 milliliter of SNOWTEX C®, available from Nissan Chemical Industries, Ltd., Houston, Tex., to 9 milliliters of deionized water. The suspension was pipetted in equal portions into three different cuvets. Solutions of 0.01 percent by weight of each of copper chloride ($CuCl_2$), iron (II) chloride ($FeCl_2$), and iron (III) chloride ($FeCl_3$), all from Aldrich Chemical Company, Milwaukee, Wis., were prepared and one drop of each was added to a separate cuvet. The Zeta Potential of all three suspensions was then measured by a Zetapals Unit. The Zeta potential of the SNOWTEX C® control suspension was measured to be −22 millivolts. The Zeta potential of the SNOWTEX C/copper chloride suspension was measured at −10 millivolts, the SNOWTEX C/iron (II) chloride suspension at −13 millivolts, and the SNOWTEX C/iron (III) chloride suspension at +13 millivolts. One drop of each of the modified nanoparticle solutions was added to a separate 2.0 milliliter solution of 0.001 percent by weight furfuryl mercaptan. High performance liquid chromatography as described in Example 1 was used to measure furfuryl mercaptan presence before and after adding the different modified nanoparticles. The results are summarized in Table 2. Each of the modified nanoparticles were successful in removing furfural mercaptan from the solution. Additionally, iron (III) ion modified silica nanoparticles had a positive Zeta Potential which can allow application to fabrics made from materials such as polypropylene, polyethylene, nylon, and cotton, which have negative value streaming potentials.

TABLE 2

| Sample | Zeta Potential | Area of furfuryl mercaptan peak | Percent of odor removed |
|---|---|---|---|
| SNOWTEX C/Cu$^{+2}$ | −10 | 3.2 maus | 97% |
| SNOWTEX C/Fe$^{+2}$ | −13 | 38 maus | 67% |
| SNOWTEX C/Fe$^{+3}$ | +13 | 3.4 maus | 97% |

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

I claim:

1. An article of manufacture, comprising:
a composition for neutralizing odor, the composition comprising a nanoparticle having a diameter of less than 500 nanometers, a surface area of at least about 500 square meters/gram, and a first Zeta Potential of about −1 to −50 millivolts, the nanoparticle comprising silica, titanium dioxide, gold, zinc oxide, polystyrene, or combinations thereof,
wherein at least one metal ion is adsorbed onto the nanoparticle, the at least one metal ion selected from the group consisting of a copper ion, a silver ion, a gold ion, and combinations thereof,
wherein the nanoparticle and at least one adsorbed metal ion is capable of binding at least one odorous compound.

2. The article of manufacture of claim 1, further comprising a second higher Zeta Potential after adsorption of the at least one metal ion onto the nanoparticle.

3. The article of manufacture of claim 1, wherein the at least one odorous compound comprises a compound selected from the group consisting of sulfur containing compounds, nitrogen containing compounds, carboxylic acids, alcohols, aliphatic aldehydes, aliphatic ketones, and combinations thereof.

4. The article of manufacture of claim 1,
wherein the nanoparticle is a silica nanoparticle; and
wherein the at least one metal ion comprises a plurality of copper ions, wherein each of the adsorbed plurality of copper ions is an active site on a surface of the silica nanoparticle for binding odorous compounds to the nanoparticle surface.

5. An article of manufacture, comprising:
a composition for removing gaseous compounds, the composition comprising a nanoparticle having a diameter of less than 500 nanometers, a surface area of greater than 200 square meters/gram, and a first Zeta Potential of about 10 to 40 millivolts, the nanoparticle comprising alumina, magnesium oxide, or combinations thereof,
wherein at least one metal ion or metal ion complex is adsorbed onto the nanoparticle, the metal ion complex selected from the group consisting of permanganate ion,
wherein the nanoparticle and at least one adsorbed metal ion or metal ion complex is capable of binding at least one gaseous compound.

6. The article of manufacture of claim 5, wherein the nanoparticle further comprises a second lower Zeta Potential after adsorption of the at least one metal ion or metal ion complex onto the nanoparticle.

7. The article of manufacture of claim 5, wherein the nanoparticle comprises a surface area of at least about 500 square meters/gram.

8. The article of manufacture of claim 5, wherein the at least one gaseous compound comprises a compound selected from the group consisting of ethylene gas, carvone, terpenoids, and combinations thereof.

9. An article of manufacture, comprising:
a composition for removal of gaseous or odorous compounds comprising a first modified nanoparticle, the first modified nanoparticle include a nanoparticle comprising a positive Zeta Potential, the nanoparticle further comprising alumina, magnesium oxide, or combinations thereof, a diameter of less than 500 nanometers, and a surface area of at least about 200 square meters/gram, the first modified nanoparticle further including at least one negatively charged metal ion complex adsorbed onto the nanoparticle, the at least one negatively charged metal ion complex selected from the group consisting of permanganate ion,
wherein the composition further comprises a second modified nanoparticle, the second modified nanoparticle including a nanoparticle comprising a negative Zeta Potential and at least one positively charged metal ion adsorbed onto the nanoparticle,
wherein the first modified nanoparticle is capable of binding a first gaseous or odorous compound and the second modified nanoparticle is capable of binding a second gaseous compound.

10. The article of manufacture of claim 9, wherein the second modified nanoparticle includes a nanoparticle comprising silica, titanium dioxide, gold, zinc oxide, polystyrene, and combinations thereof; and
wherein the at least one positively charged metal ion comprises a metal ion selected from the group consisting of copper ion, silver ion, gold ion, iron ion, and combinations thereof.

11. An article of manufacture, comprising:
a modified nanoparticle comprising a nanoparticle having a diameter of less than 500 nanometers and a surface area of at least about 500 square meters/gram, the nanoparticle comprising silica, alumina, magnesium oxide, titanium dioxide, iron oxide, gold, zinc oxide, copper oxide, polystyrene, or combinations thereof; and at least one metal ion or metal ion complex adsorbed onto the nanoparticle material, the at least one metal ion or metal ion complex comprising an ion or ion complex selected from the group consisting of a copper ion, a silver ion, a gold ion, a permanganate ion, an iron ion, and combinations thereof;
wherein the nanoparticle comprises a first Zeta Potential before adsorption of the metal ion or metal ion complex and a second Zeta Potential after adsorption, wherein the difference between the first Zeta Potential and the second Zeta Potential is at least about 5.0 millivolts;
wherein the modified nanoparticle is capable of binding at least one odorous or gaseous compound to the modified nanoparticle.

12. The article of manufacture of claim 11, wherein the second Zeta Potential is determined by an add-on amount of adsorbed metal ions.

13. The article of manufacture of claim 11, wherein the nanoparticle comprises a first Zeta Potential of about 1 to 70 millivolts.

14. The article of manufacture of claim 11, wherein the nanoparticle comprises a first Zeta Potential of about −1 to −50 millivolts.

15. The article of manufacture of claim 11,
wherein the nanoparticle is a silica nanoparticle; and
wherein the at least one metal ion comprises a plurality of copper ions, wherein each of the adsorbed plurality of copper ions is an active site on a surface of the silica nanoparticle for binding odorous compounds to the nanoparticle surface.

16. The article of manufacture of claim 11, wherein the modified nanoparticle is adsorbed onto the article of manufacture by an electric potential difference between the modified nanoparticle and the article of manufacture.

17. The article of manufacture of claim 11, wherein the article of manufacture comprises an absorbent article.

18. The article of manufacture of claim 17, wherein the absorbent article comprises a diaper.

19. The article of manufacture of claim 17, wherein the absorbent article comprises a feminine hygiene product.

20. The article of manufacture of claim 11, wherein the article of manufacture comprises a paper towel.

21. The article of manufacture of claim 11, wherein the article of manufacture comprises a household air freshener.

22. The article of manufacture of claim 11, wherein the article of manufacture comprises an oral hygiene product.

23. The article of manufacture of claim 11, wherein the article of manufacture comprises a wipe.

24. The article of manufacture of claim 11, wherein the article of manufacture comprises a fibrous cloth.

25. The article of manufacture of claim 11, wherein the article of manufacture comprises an air filter.

26. The article of manufacture of claim 11, wherein the article of manufacture comprises an odor adsorbing powder.

* * * * *